US009138005B2

(12) United States Patent
Berentsveig et al.

(10) Patent No.: US 9,138,005 B2
(45) Date of Patent: Sep. 22, 2015

(54) MEMBRANE CONCENTRATOR

(71) Applicant: SABAN VENTURES PTY LIMITED, Alexandria (AU)

(72) Inventors: Vladimir Berentsveig, Alexandria (AU); Ron Weinberger, Alexandria (AU)

(73) Assignee: Saban Ventures Pty Limited, Alexandria, New South Wales (AU)

( * ) Notice: Subject to any disclaimer, the term of this patent is extended or adjusted under 35 U.S.C. 154(b) by 86 days.

(21) Appl. No.: 14/151,364

(22) Filed: Jan. 9, 2014

(65) Prior Publication Data

US 2014/0219866 A1 Aug. 7, 2014

Related U.S. Application Data

(62) Division of application No. 11/997,886, filed as application No. PCT/AU2006/001116 on Aug. 4, 2006, now Pat. No. 8,658,089.

(30) Foreign Application Priority Data

Aug. 4, 2005 (AU) ................................ 2005904181
Aug. 4, 2005 (AU) ................................ 2005904196
Aug. 4, 2005 (AU) ................................ 2005904198
Feb. 15, 2006 (AU) ................................ 2006900748

(51) Int. Cl.
*A61L 9/00* (2006.01)
*A01N 59/00* (2006.01)
(Continued)

(52) U.S. Cl.
CPC ................ *A01N 59/00* (2013.01); *A01N 25/06* (2013.01); *A61L 2/06* (2013.01); *A61L 2/16* (2013.01);
(Continued)

(58) Field of Classification Search
CPC ............. A61L 2/00; A61L 2/186; A61L 2/22; B01B 1/005
USPC .......................................................... 422/1, 4
See application file for complete search history.

(56) References Cited

U.S. PATENT DOCUMENTS 3,476,506 A 11/1969 Andersen et al.
3,481,689 A 12/1969 Rosdahl et al.
(Continued)

FOREIGN PATENT DOCUMENTS

EP 0679407 A2 11/1995
GB 663720 12/1951
(Continued)

OTHER PUBLICATIONS

International Search Report, PCT/AU2006/001116, dated Sep. 1, 2006, 4 pages.
(Continued)

*Primary Examiner* — Monzer R Chorbaji
(74) *Attorney, Agent, or Firm* — Senniger Powers LLP

(57) ABSTRACT

Apparatus for concentrating a nebulant comprising a nebulant flow conduit and a counter-flow conduit, or preferably, a plurality of alternating nebulant flow conduits and corresponding counter-flow conduits eg in layered or coaxial arrangement. and wherein at least a portion of the nebulant flow conduit and said counter-flow conduits define respective opposed sides of a gas permeable membrane. In use a nebulizer is in communication with the nebulant flow conduit and the nebulant flow and counter-flow are in the same or opposite directions and act to concentrate the amount of active in a droplet eg from 35 wt % to 60 wt % hydrogen peroxide in water to disinfect and/or sterilize an article.

16 Claims, 9 Drawing Sheets

(51) Int. Cl.
| | |
|---|---|
| *A01N 25/06* | (2006.01) |
| *A61L 2/06* | (2006.01) |
| *A61L 2/20* | (2006.01) |
| *A61L 2/22* | (2006.01) |
| *A61L 2/24* | (2006.01) |
| *C01B 15/013* | (2006.01) |
| *A61L 2/16* | (2006.01) |

(52) U.S. Cl.
CPC . *A61L 2/20* (2013.01); *A61L 2/208* (2013.01); *A61L 2/22* (2013.01); *A61L 2/24* (2013.01); *C01B 15/013* (2013.01); *A61L 2202/24* (2013.01)

(56) References Cited

U.S. PATENT DOCUMENTS

| | | | |
|---|---|---|---|
| 3,950,247 | A | 4/1976 | Chiang et al. |
| 4,022,324 | A | 5/1977 | Schuster |
| 4,191,543 | A | 3/1980 | Peters |
| 4,296,068 | A | 10/1981 | Hoshino |
| 4,366,125 | A | 12/1982 | Kodera et al. |
| 4,680,163 | A | 7/1987 | Blidschun et al. |
| 4,718,985 | A | 1/1988 | Kjellander |
| 4,744,951 | A | 5/1988 | Cummings et al. |
| 4,958,529 | A * | 9/1990 | Vestal ............... 73/864.81 |
| 4,978,430 | A | 12/1990 | Nakagawa et al. |
| 5,454,274 | A | 10/1995 | Zhu |
| 5,611,842 | A | 3/1997 | Friesen et al. |
| 5,843,209 | A | 12/1998 | Ray et al. |
| 5,851,485 | A | 12/1998 | Lin et al. |
| 6,066,294 | A | 5/2000 | Lin et al. |
| 6,325,972 | B1 | 12/2001 | Jacobs et al. |
| 6,379,616 | B1 | 4/2002 | Sheiman |
| 6,500,465 | B1 | 12/2002 | Ronlan |
| 6,656,426 | B1 | 12/2003 | Wang et al. |
| 6,977,061 | B2 | 12/2005 | Lin et al. |
| 7,014,813 | B1 | 3/2006 | Watling et al. |
| 7,122,166 | B2 | 10/2006 | Parrish |
| 7,326,382 | B2 | 2/2008 | Adiga et al. |
| 2002/0119075 | A1 | 8/2002 | Jacobs et al. |
| 2002/0192110 | A1 | 12/2002 | Garlick |
| 2003/0143110 | A1 | 7/2003 | Kritzler et al. |
| 2003/0183576 | A1 | 10/2003 | Ohara et al. |
| 2003/0192799 | A1 | 10/2003 | Addy et al. |
| 2004/0022673 | A1 | 2/2004 | Protic |
| 2004/0062692 | A1 | 4/2004 | Lin et al. |
| 2005/0084415 | A1 | 4/2005 | McVey et al. |
| 2005/0252856 | A1 | 11/2005 | Parrish |

FOREIGN PATENT DOCUMENTS

| | | |
|---|---|---|
| GB | 1138512 | 1/1969 |
| GB | 2346095 A | 8/2000 |
| JP | 55-137007 | 10/1980 |
| JP | S60220067 | 2/1985 |
| JP | 60-206408 | 10/1985 |
| JP | 63-175602 | 7/1988 |
| JP | 02-273518 | 11/1990 |
| JP | 10-284458 | 10/1998 |
| JP | 2003-095617 | 4/2003 |
| JP | 2003-180802 | 7/2003 |
| JP | 2004-267755 | 9/2004 |
| JP | 2006519780 A | 8/2006 |
| WO | 9111374 A2 | 8/1991 |
| WO | 9602316 A1 | 2/1996 |
| WO | 9966961 A1 | 12/1999 |
| WO | 0121223 A1 | 3/2001 |
| WO | 02056988 A2 | 7/2002 |
| WO | 2004073827 A1 | 9/2004 |

OTHER PUBLICATIONS

International Preliminary Report on Patentability, PCT/AU2006/001116, dated Jul. 30, 2007, 3 pages.

McDonnell, G., et al., "Antiseptics and Disinfectants: Activity, Action, and Resistance," 1999, Clin Microbiol Rev, 12/1:147-179.

Content and Format of Premarket Notification [510(k)] Submissions for Liquid Chemical Sterilants/High Level Disinfectants, Jan. 3, 2000, Guidance for Industry and FDA Reviewers, CDRH, 59 pages.

English translation of Office Action issued in Japanese Patent Application No. 2008-524316, mailed Nov. 29, 2011, provides brief description of JP S60220067 for which no English translation is available. 5 pages.

"Explanation of HMIS Ratings," obtained from http://www.paint.org/component/docman/cat_view/49-hmis.html on Feb. 10, 2012, 2 pages.

Material Safety Data Sheet, Peracetic Acid, 35% MSDS, Sciencelab.com, created Oct. 10, 2005, Updated Nov. 1, 2010, 7 pages.

Material Safety Data Sheet, Hydrogen Peroxide Solutions Greater Than 60%, FMC MSDS Ref. No. 7722-84-1-5, Date Approved May 21, 2011, Revision No. 12, 11 pages.

Material Safety Data Sheet, Ethanol Solution, Sigma-Aldrich Corporation, Version 3.1, Revised Jul. 12, 2011, Printed Feb. 10, 2012, 7 pages.

Abstract of JP 2002-201004, Toyota Motor Corp., Jul. 16, 2002, 1 page.

\* cited by examiner

FIGURE 2

FIGURE 6
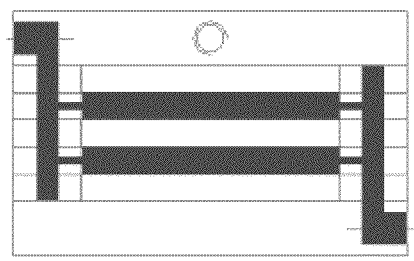
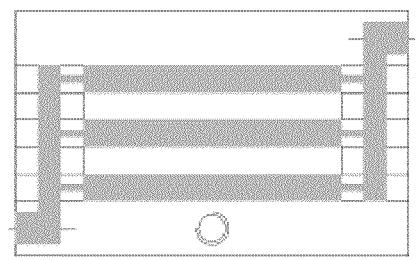
Nanonebulant Flow
Pathway
Counter Flow
Pathway

MEMBRANE CONCENTRATOR

REFERENCE TO CORRESPONDING APPLICATIONS

The present application is a division of U.S. application Ser. No. 11/997,886, issued as U.S. Pat. No. 8,658,089, which is a U.S. National Stage Application of International Application No. PCT/AU2006/001116, filed Aug. 4, 2006, and claims priority to Australian Patent Application Nos. 2005904181, 2005904196, and 2005904198, all filed Aug. 4, 2005, and Australian Patent Application No. 2006900748, filed Feb. 15, 2006, the entire contents of which are incorporated herein by reference.

FIELD OF THE INVENTION

This invention relates to a method and apparatus for concentrating aerosols, such as may be used for example in disinfecting or sterilizing a surface. The method and apparatus are particularly suited for disinfecting or sterilizing medical instruments but are not limited to that use.

BACKGROUND OF THE INVENTION

The present application incorporates by reference the whole of the applicants co-pending applications AU2005904181, AU 2005904196 and AU 2005904198.

As outlined in these co-pending applications, sterilization processes and apparatus that address the following criteria are highly desirable:
(a) avoid the need for vacuum
(b) avoid the need for a rinsing step
(c) avoid the need for temperatures above 60° C.

Many of the process of the prior art employ vacuum and or rinsing steps. These have the effect of increasing the complexity and cost of the apparatus required, and can lengthen the time of the disinfection or sterilization process considerably (meaning more downtime for expensive medical instruments). The use of high temperatures can also increase the complexity and cost of sterilization instruments, but more importantly, it can damage many materials.

It is desired to provide disinfecting methods and apparatus that meet these criteria, while achieving the highest possible efficacy in pathogen destruction, especially when treating occluded, mated and lumen surfaces.

It is desirable that the disinfecting methods use hydrogen peroxide. Hydrogen peroxide at low concentrations is safe to transport, sell and handle and is extremely well known, with little or no regulatory barriers to its use. However, there are problems with those methods which require high concentration hydrogen peroxide as a starting material. For example, commercial vapour and plasma processes use as a starting material corrosive and irritating 60% peroxide solutions which requiring special packaging and handling precautions.

When hydrogen peroxide is used in the form of small droplets (sprayed, ultrasonically nebulized, etc), the particles have a tendency to deposit as droplets on surfaces and the residual layer of peroxide is a potential problem. Medical instruments, food packaging and other disinfected items need to be stored dry to avoid re-contamination. Importantly, surgical instruments must not contain residual peroxide at levels higher than 1 microgram/sq·cm.

However, eliminating residual peroxide is very difficult. It requires either washing which introduces the associated problems previously discussed in our copending applications in connection with liquid systems, prolonged periods of high temperature drying (which completely negate any advantages arising from fast kill times and low process temperature) or requires use of catalase or other chemical means to decompose peroxide (which still requires drying and which creates a series of problems with the residual chemicals left on instruments) or the use of vacuum. Accordingly, it is desirable to provide a system that uses the minimum possible amount of peroxide to achieve a desired effect.

Any discussion of the prior art throughout the specification should in no way be considered as an admission that such prior art is widely known or forms part of common general knowledge in the field.

OBJECTS OF THE INVENTION

It is an object of the invention to provide improved methods and apparatus for disinfecting or sterilizing medical instruments which avoids or ameliorates at least some of the disadvantages of the prior art.

It is an object of preferred embodiments of the invention to provide improved methods an apparatus capable of concentrating and improving the properties of an aerosol.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Brief Statement of Invention

According to a first aspect, the present invention provides apparatus for concentrating a nebulant comprising:
a nebulant flow conduit;
a counter-flow conduit; and
wherein at least a portion of said nebulant flow conduit and said counter-flow conduit define respective opposed sides of a gas permeable membrane.

According to a second aspect, the present invention provides apparatus for concentrating a nebulant comprising:
a plurality of alternating nebulant flow conduits and corresponding counter-flow conduits; and
wherein at least a portion of said each nebulant flow conduit and an adjacent counter-flow conduit define respective opposed sides of a gas permeable membrane.

The alternating nebulant flow conduits and counter-flow conduits may be in a layered configuration. Alternatively, they maybe in a concentric, coaxial tubular arrangement.

Each nebulant flow conduit comprises an inlet and an outlet. Each counter-flow conduit comprises an inlet and an outlet. Preferably, the nebulant flow and counterflow are in opposite directions. However, they may in the same direction, or any other direction, eg perpendicular flows.

According to a third aspect the invention provides apparatus for concentrating a nebulant comprising:
a nebulant flow conduit;
at least two counter-flow conduits; and
wherein at least a portion of said nebulant flow conduit and said counter-flow conduits define respective opposed sides of gas permeable membranes.

According to a fourth aspect the invention provides apparatus for concentrating a nebulant comprising:
at least two nebulant flow conduits;
a counter-flow conduit; and
wherein at least a portion of said counter-flow conduit and said nebulant flow conduits define respective opposed sides of gas permeable membranes.

According to a fifth aspect the present invention provides a method for concentrating a nebulant comprising the steps of (1) providing a nebulant flow of an active in a solvent and having a first active:solvent ratio to a first side of a gas permeable membrane; and (2) providing a counter-flow of a gas to a second side of the gas-permeable membrane whereby to increase said ratio on the first side to a second active:solvent ratio greater than the first active:solvent ratio.

The concentrated nebulant is preferably used to disinfect and/or sterilize an article.

The nebulant is preferably a nebulant of water and a biocide. Most preferably, the biocide is hydrogen peroxide. The first active to solvent ratio is preferably about 30 wt %.

The second active:solvent ratio is preferably about 70 wt %. The counter-flow of gas is provided at a rate and for a time such that the second ratio is not capable of further increase.

For preference the gas is air, more preferably humidity conditioned air.

The semi permeable fabric or membrane may be a woven, or non-woven fabric, or it may be a sheet or film or a combination thereof and may be of a single layer or multilayer construction.

The term "semi permeable membrane" is used herein where the context permits to include all such fabrics and membranes having the selected properties. The semi permeable membrane may be hydrophobic or hydrophilic in nature.

The semi permeable membrane is selected to ensure that nebulant particles are initially unable to permeate.

In this specification where the context permits references to a semi permeable fabric or membrane include fabrics or membranes suitable for pervaporation as well those only suitable for simple permeation, and references to permeation include references to pervaporation. Other membranes than those described and membranes may be used and may include membranes suitable for pervaporation.

In a highly preferred embodiment a peroxide solution having an initial concentration of at least 6%, preferably 20%-35%, and more preferably 30%-35%, is nebulized. Preferably the solution is nebulized in an ultrasonic nebulizer operated at 2.4 MHz which generates an aerosol in which particles having a size range distribution of about 1-10 microns are suspended in an air stream. As herein used the term "nebulant" describes droplets of liquid (i.e. finely divided liquid particles) entrained in a gas stream. A system of liquid droplets entrained or suspended in a gas is an "aerosol".

Without wishing to be bound by theory, it is believed that as water vapour permeates through the membrane, water evaporates from the nebulant droplets in order to restore the equilibrium vapour pressure within the nebulant flow conduit. Continuing evaporation from the droplets results in the peroxide solution in the nebulant becoming more concentrated, and in the droplets shrinking in size.

These smaller more concentrated nebulant particles are significantly more effective as a sterilant than prior art hydrogen peroxide vapour possibly because a much higher concentration of sterilant is obtainable per unit volume than with vapour and is more effective than prior art peroxide nebulant sterilants and processes.

Air permeating into the nebulant flow conduit is sterile by virtue that the membrane is not penetrable by micro-organisms.

According to a sixth aspect the invention provides a process according to any one of the preceding aspects wherein the semi permeable membrane is selected to remove one or more vapours by a process of pervaporation.

Although the invention is herein described with reference to hydrogen peroxide as the biocide, the invention is equally applicable when the biocide was another peroxide or peroxy compound, or could be used with other known vaporizable biocides or biocides when dissolved in suitable solvents (which need not be aqueous). Furthermore, although it is highly preferred to introduce the biocide as an aerosol, in less preferred embodiments the biocide can be introduced as a vapour and the vapour subsequently removed at atmospheric pressure by an exterior current of air (or other fluid) adjacent the membrane exterior. Introduction of the biocide as an aerosol is greatly preferred because much higher initial densities of biocide per liter of container can be achieved than with a vapour. Our co-pending application indicates that aerosols according to that invention, which are believed to be the same as or similar to the aerosols produced in this process are more effective than vapour.

According to a seventh aspect the present invention provides a method for disinfecting or sterilizing an article or article part comprising the steps of (1) enclosing the article or article part inside a first container having a wall of which at least a part is a semi permeable fabric or membrane;

(2) the semi permeable fabric or membrane being selected to allow vapour to pass from inside to outside of the container while providing a barrier against entry of micro-organisms and against exit of nebulant particles;

(3) admitting a biocide solution comprising a biocide dissolved in a solvent to a second container;

(4) concentrating the biocide in the second container by removal of solvent, to form a concentrated biocide (5) introducing the concentrated biocide as a liquid or a vapour or a combination thereof from the second container to the first; and wherein steps (4)-(5) are conducted at or above atmospheric pressure.

In preferred embodiments according to the sixth aspect a hydrogen peroxide solution in water of for example 35% concentration is firstly concentrated as a nebulant in one chamber by removal of water through a membrane at atmospheric pressure. The concentrated nebulant is then admitted to another chamber which is desirably a bag or other container having a semi permeable membrane as defined as a wall or part thereof which is then sealed. This allows the article to be sterilized and stored sterile in the second container and permits removal of residual hydrogen peroxide and water. Preferably the invention provides in particular, a nanonebulant having 90% of particles in the 3-5 μm range and a peroxide concentration of >70 wt % and a water concentration of less than 30 wt %.

According to an eighth aspect the invention consists in a nano-nebulant comprising a solution of hydrogen peroxide suspended in finely divided form wherein the liquid particles have concentration of greater than 60 wt % of hydrogen peroxide, and an average diameter of less than 1.0 micron. Preferably the droplets have an average diameter of less than 0.8 microns.

It will be appreciated that in prior art aerosol systems the peroxide liquid particles have had a concentration of less than 35% wt of hydrogen peroxide and an average diameter in excess of 2 microns. The relationship between particle size and fall velocity of particles in an aerosol is non linear, and so a small reduction in particle diameter greatly increases suspension stability as well as increasing the total surface area of the gas/liquid interface.

Desirably, the nebulant according to the seventh aspect has a peroxide density (grams of hydrogen peroxide/liter of aerosol) much greater than the peroxide density of a vapour at just below its saturation limit at a corresponding temperature and humidity.

BRIEF DESCRIPTION OF THE DRAWINGS

FIG. 2 is diagram of a first simple embodiment of the present invention.

FIG. 6 shows flow patterns of nebulant and counter flow in an embodiment of the present invention

DESCRIPTION OF PREFERRED EMBODIMENTS

The invention will now be described in the context of sterilization, but it will be appreciated that the pre-concentrators and pre-concentration methods of the present invention can be used in a variety of fields where concentrated nebulants are desired, eg drug delivery, painting/printing, food preparation, materials fabrication and the like. For example, a number of such processes have been described (U.S. Pat. No. 6,451,254, U.S. Pat. No. 6,673,313 and U.S. Pat. No. 6,656,426) all of which require involve concentrating a hydrogen peroxide solution by lowering the pressure to preferentially evaporate water and removing the water through a vacuum pump prior to vaporising the solution.

Figure 1:
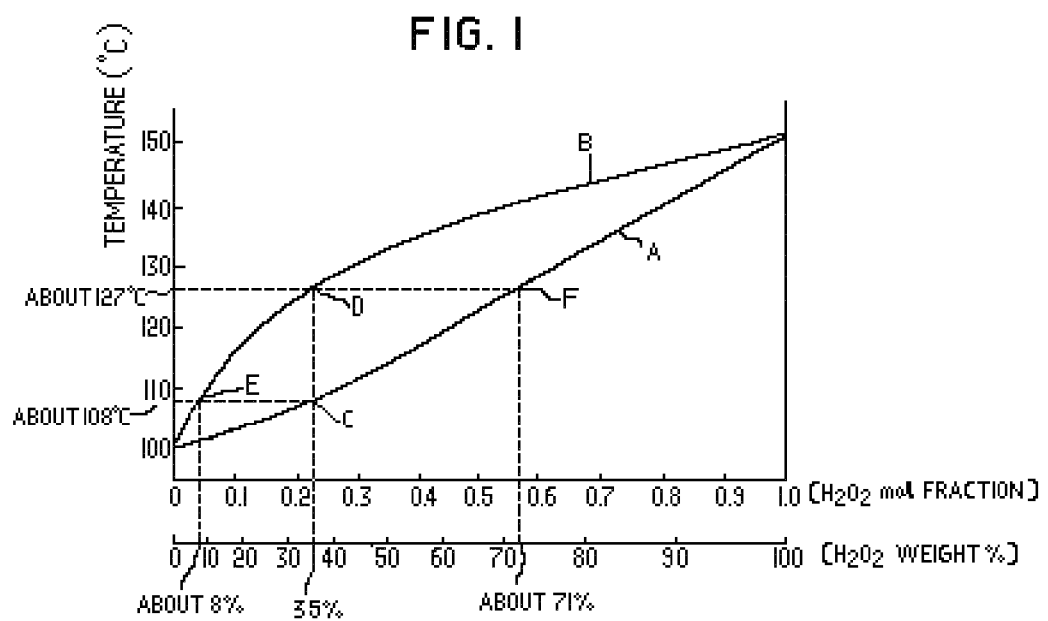
FIG. 1 is a reproduction of a figure from U.S. Pat. No. 4,797,255 which shows (curve A) how the boiling point of a water/peroxide mixture changes with concentration at atmospheric pressure and (curve B) how the gas composition changes.
Figure 3:
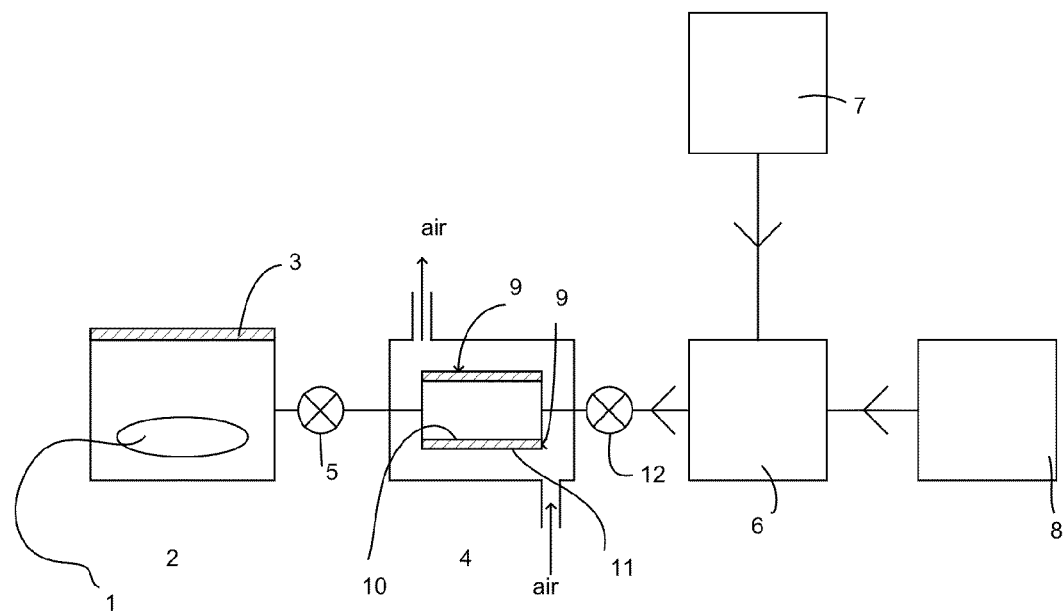
FIG. 3 is a diagram of a sterilizing apparatus showing the pre-concentrator of the present invention

The general pre-concentration process of the present takes place in the context of the following, and can be seen with reference to FIG. 3. An article to be sterilized 1 is placed into a sterilization chamber 2. The sterilization chamber 2 may be any suitable container, but advantageously is a bag made from a semi-permeable membrane, or a sealed container having a window of a semi-permeable membrane 3.

A pre-concentrator chamber of the present invention 4 is connected upstream of the sterilization chamber 2. The sterilization chamber 2 and pre concentrator 4 are connected such that flow between the pre-concentrator and sterilizing chamber can be opened or closed by way of a valve 5.

An ultrasonic nebulizer 6 is connected upstream of the pre-concentrator chamber. A hydrogen peroxide solution having a starting concentration preferably of around 30-35% is nebulized in an ultrasonic nebulizer.

The nebulizer 6 may be fed with sterilant solution on a continuous or intermittent basis from a bulk supply 7, e.g. while maintaining a predetermined liquid level in the nebulizer, or may be provided with a single shot dosing system for example a cartridge providing sufficient solution for one or a plurality of sterilization cycles. Alternatively, a sterilant solution may be provided pre-packed in a capsule which may be placed in an adapted nebulizer so that the capsule is in contact with the ultrasonic transducer of the nebulizer. In this case means are provided for piercing the capsule so that it is able to release the solution as a nebulant. In another embodiment the sterile solution may be provided in a capsule having an integral ultrasonic transducer adapted to be energised via contacts extending through the capsule wall when the capsule is inserted in the nebulizer.

The nebulizer 6 need not be ultrasonic, and any other means for forming an aerosol could be used including sprays, jets, and other devices. It is conceivable that peroxide could be pre-packed and stored as an aerosol in an aerosol container and could be admitted from the aerosol container. It is also envisaged that cassettes incorporating an ultrasonic transducer could be used to generate an aerosol in-situ within the enclosed container which would be provided with electrical connections to the exterior to provide for energisation and control.

The nebulizer 6 operates preferably at around 2.4 MHz to form an aerosol with typically more than 90% of the droplets being between 1 and 10 µm in diameter, with the median size being around 3-5 µm in diameter ("micro particles")

Although the present invention has been described with reference to nebulization by means of an ultrasonic nebulizer, it will be understood that other means for nebulization including sprays, jet nebulizers, piezoelectric nebulizers, and such like nebulant generating devices may be employed. As described in our co-pending application (PCT/AU99/00505), smaller particles can be obtained by including a surfactant for example an alcohol, in the sterilant solution when using ultrasonic nebulization. It is not necessary for an ultrasonic nebulizer to be run continuously and in preferred embodiments of the invention the nebulizer is switched on and off cyclically, (or at irregular intervals) being run for example about 20 seconds per minute.

The aerosol or nebulant of microparticles is then propelled into the pre-concentrator 4 by means of a fan 8 upstream of the nebulizer 6. The microparticles formed by the nebulizer 6 are entrained in a gas stream which in the preferred embodiment is air. It is a significant advantage of preferred embodiments of the invention over prior art that they do not require a source of filtered sterile air. Instead the invention is able to draw non-sterile air from the sterilization chamber, and sterilize it while recirculating it in use. However, if preferred, aseptic filtered air could be employed. The gas stream is not necessarily air, and could for example be an inert gas such as nitrogen, or argon; or could be oxygen or ozone.

In general terms, the pre-concentrator 4 works by exposing the aerosol droplets to one face 10 of a semi permeable membrane 9 while an air current moves across the other face 11 of this semi permeable membrane. This leads to preferential evaporation of the water from the aerosol droplets, causing them to become more concentrated with respect to hydrogen peroxide. As a result of the preferential evaporation of water, the aerosol droplets inside the pre concentrator 4 become more concentrated with respect to hydrogen peroxide with the concentrations approaching 60% or upwards. Water continues to preferentially evaporate from the droplets until this maximum hydrogen peroxide concentration is achieved, after which peroxide and water evaporate in an equilibrium fixed proportion.

Once formed, the small highly concentrated droplets then make contact with the article to be sterilised.

There are two possible preferred modes of operation of the pre-concentrator:

In the first operating mode, which is a batch-wise concentration process, the pathway between the concentrator 4 and sterilizing chamber 2 is shut and an aerosol of a solution of 35% hydrogen peroxide in water with droplet sizes between 1 and 10 µm is driven into the pre-concentrator chamber 4. The pre-concentrator chamber is then isolated (by shutting both valves 5 and 12) and the aerosol in the pre-concentrator 4 is then concentrated. Concentration in the pre-concentrator takes place until the maximum concentration of peroxide is achieved, beyond which peroxide and water evaporate in an equilibrium fixed proportion. Once this maximum concentration is achieved, the pathway between the pre-concentrator and sterilizing chamber is opened by opening valve 5 and the concentrated nebulant is introduced into the sterilization chamber 2.

In the second alternative operating mode, which is a continuous concentration process, the pathway between the pre-concentrator 4 and the sterilization chamber 2 is left open. An aerosol of a solution of 35% hydrogen peroxide in water with droplet sizes between 1 and 10 μm enters the pre-concentrator chamber 4 and passes continuously through the pre-concentrator with fan 8 propulsion. As the aerosol droplets pass through the pre-concentrator 4, the water is preferentially removed. Residence time of the droplets in the pre-concentrator is such that the maximum possible concentration of peroxide is achieved by the time they exit the pre-concentrator.

The nebulant may be introduced into the pre-concentrator 4 continuously or intermittently, for example, 2 secs on/18 secs off; or 5 secs on/15 secs off; over a period of, for example, 2 minutes.

However, regardless of whether batch-wise mode a) or continuous mode b) is employed, or even should some combination of continuous or batch wise modes be used, the aerosol droplets that exit the pre-concentrator 4 and enter the sterilization chamber 2 are at their maximum achievable hydrogen peroxide concentration.

As the concentration of hydrogen peroxide in the droplets increases, the proportion of hydrogen peroxide in the vapour in equilibrium with the droplets increases.

Once the concentrated nebulant is introduced to the sterilization chamber 2, it contacts the article to be sterilized 1 and acts upon the pathogens at the surface. The sterilizing chamber 2 may then be sealed from the pre-concentrator 4. Because the peroxide concentration is at a maximum, no further concentration of the peroxide solution takes place in the sterilizing chamber 2. Any vaporization in the sterilization chamber takes place such that peroxide and water evaporate in an equilibrium fixed proportion. The concentrated biocide is then allowed to contact the article to be sterilized. The article to be sterilized can be stored in the sterilization chamber until needed. This also permits removal of residual hydrogen peroxide and water.

Figure 4:
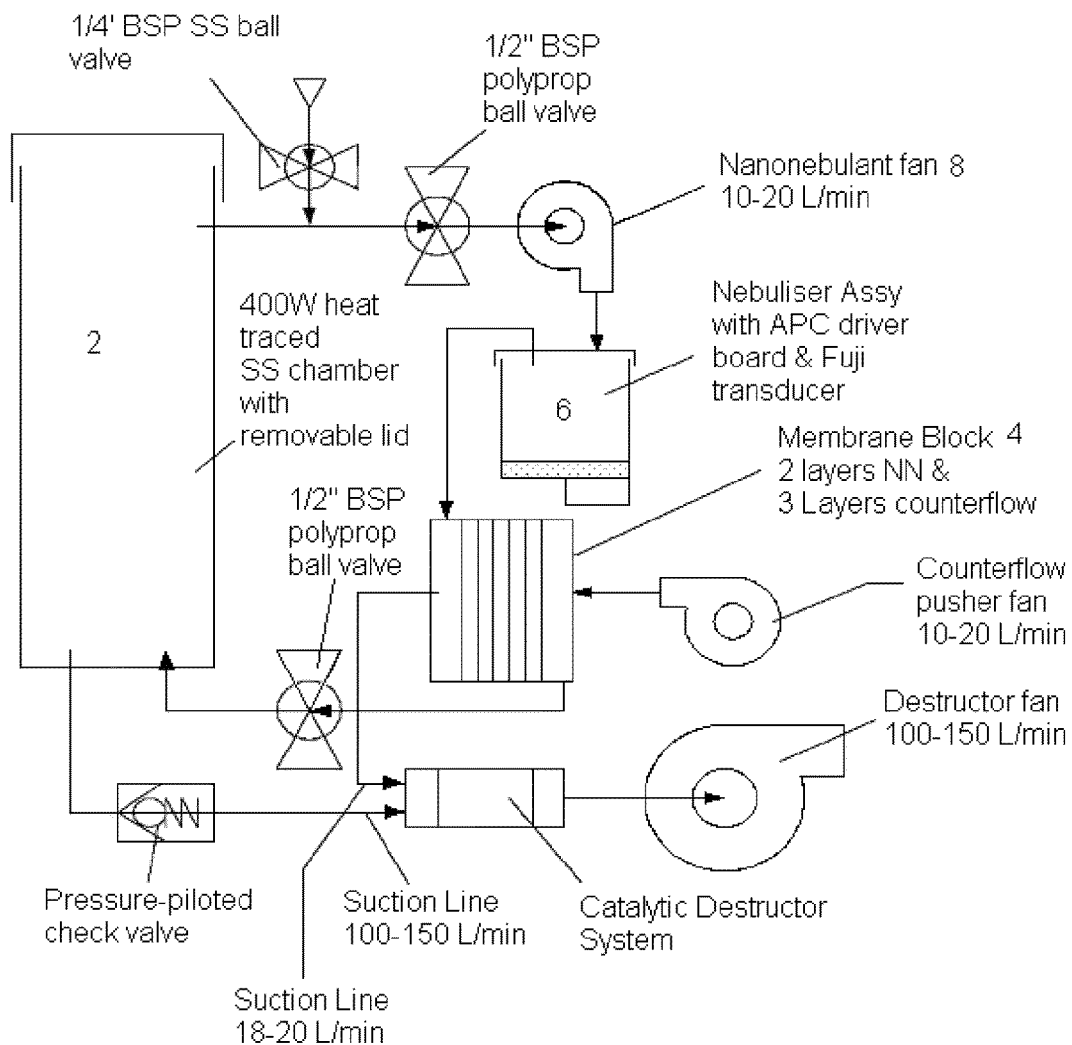
FIG. 4 is a more detailed schematic diagram of a sterilizing apparatus showing the pre-concentrator of the present invention

To expand on each of the steps, and shown in FIG. 4, the cycle commences with nebulization of 27-35% hydrogen peroxide into micro droplets inside a nebulization chamber 6 using an ultrasonic piezo ceramic transducer that vibrates at 2.4 MHz. The transducer may function continuously or according to an appropriate duty cycle such that nebulization is intermittent. The nebulant mist has micro-droplets which have the same composition as the bulk solution from which they were derived.

Once produced, the nebulant mist is transported by a blower fan 8 into the membrane concentrator system 4 where it is concentrated by means of evaporation into sub-micron particles or nano-nebulant.

The membrane concentrator 4 is preferably a multi-layered device where nebulant flows over membrane layers which have an alternate airflow on the other side. Selective removal of a proportion of the water vapor from the nebulant occurs in the membrane concentrator due to the differential partial pressures of water and hydrogen peroxide. The concentrator may be electrically heated if required to provide the desired effect. Not only do the droplets become more concentrated (~60-70%), because of the loss of solvent (water) they become smaller. The smaller droplets also increase surface area/volume and so become more stable. The net result is an ultra-fine, stable and concentrated mist or nano-nebulant. At the exit point of the concentrator the mist is "terminally" concentrated such that no further concentration of hydrogen peroxide occurs in the sterilization chamber.

Figure 2:
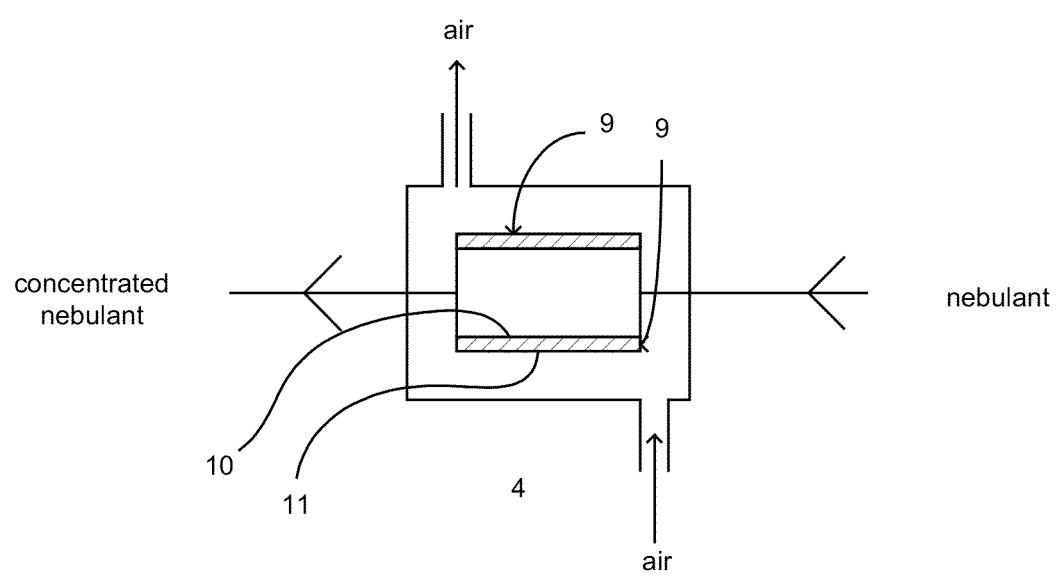
Figure 5:
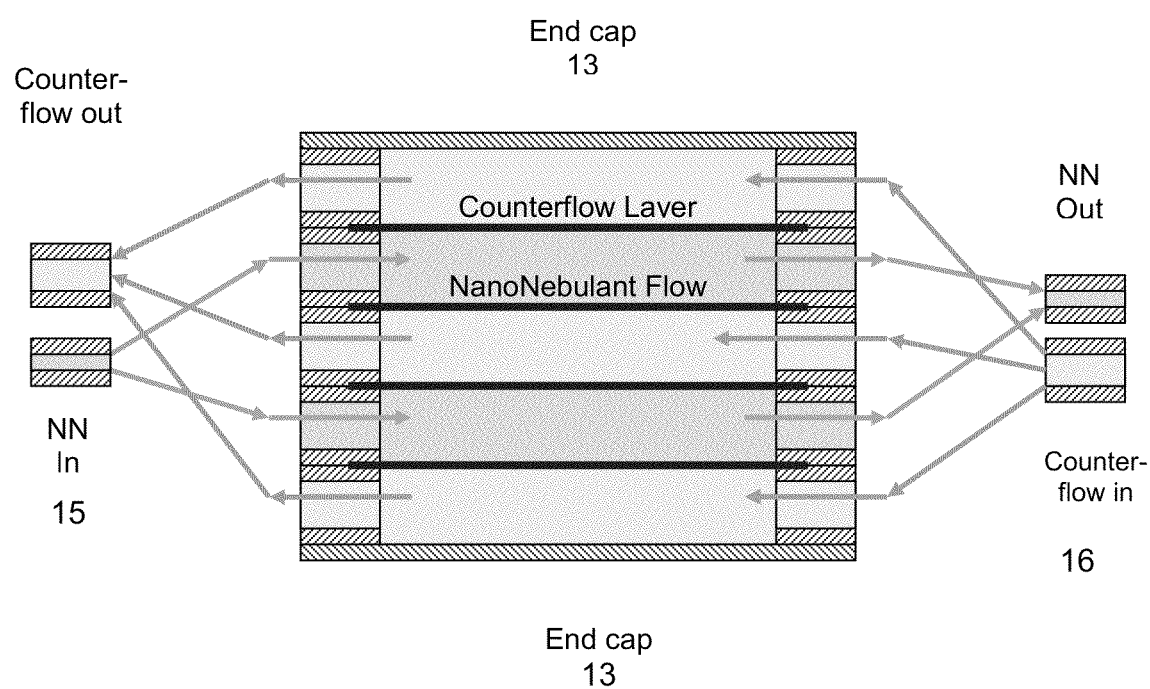
FIG. 5 shows a further embodiment of the present invention.
Figure 7:
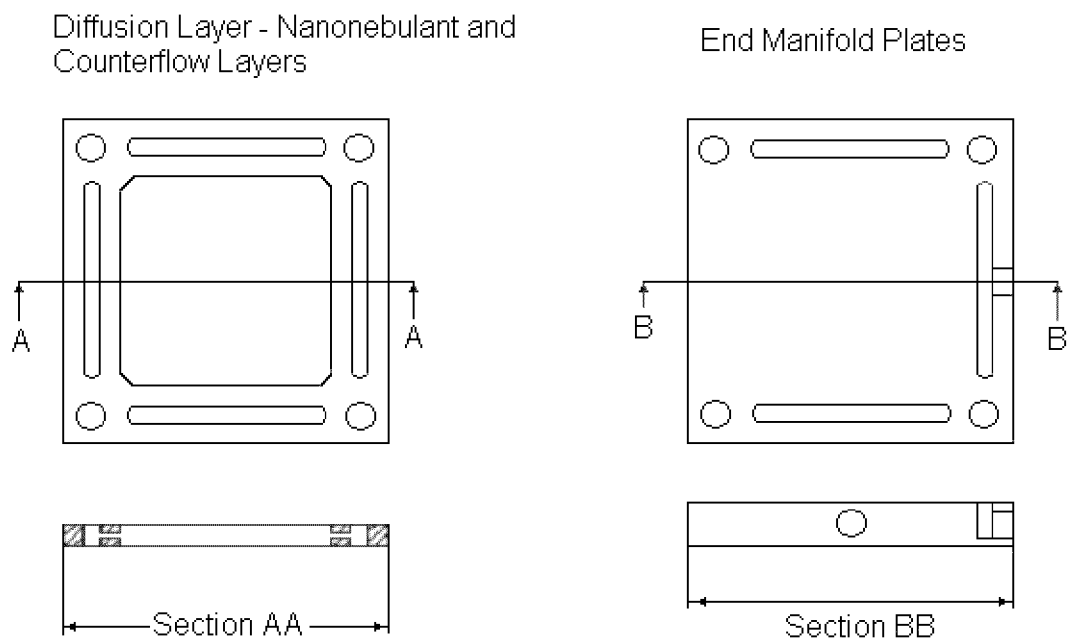
FIG. 7 shows the plates that may be used to separate semi permeable membranes in those embodiments of the present invention that use stacked arrays.

In one simple embodiment, seen in FIG. 2, the membrane concentrator is a modular, stackable assembly consisting of 4 main components—flow layer, end plate, tie-rod and membrane sheet. FIG. 5 shows a preferred stack of concentrator modules.

The flow layers 10 and 11 are defined by thin, square or rectangular plates 12 with a large open area inside and four slots (galleries) running parallel to the outer edges, two of which are connected to the inner space via slots. The orientation of the flow layers (when using square sections), determines the number of layers which are common to any particular gallery, hence two distinct flow lines may operate an one single assembly through the method of assembly.

The end plates 13 allow connection of external tubing or devices to the membrane assembly and each end plate has two connection points which correspond to two gallery slots. The slots on these end plates form a manifold which directs flow up one particular gallery per connection and the connections are offset 90 degrees from one another to ensure they access different galleries.

When five flow layers, for example are stacked atop one another with alternate orientations i.e. 90 degrees to each other, and separated by sheets of membrane material, they form two groups of flow layers, one having two flow layers 15 and the other having three separate flow layers 16 within the block. These flow layers are assigned to either nano-nebulant (15 in the present case) or crossflow/counterflow (16 in the present case) connections and through regulation of their flow rates, controlled diffusion is possible.

The tie-rods are used to compress the layers between the end plates and create a vapor seal, although any design which allows the blocks to fit together in suitable sealed arrangement may be used. The membrane material 9 also acts as a gasket between the layers.

Whilst the vapour pressure of hydrogen peroxide at ambient temperatures is negligible, and water preferentially evaporates in the membrane concentrator, as a precaution against any hydrogen peroxide flow exiting the system, the counter flow is taken directly into the catalytic destructor module where it is safely treated.

The semi-permeable membrane 9 in the present example is preferably made of KIMGUARD™, a three layer non linting laminate fabric using polypropylene and having an inner layer which is hydrophobic and resistant to bacterial penetration. The two outer layers provide abrasion resistance and strength. As a multi layered fabric it has no actual pore size, but the fabric is permeable by virtue of microscopic channels which provide a tortuous path limiting passage of particles to those of less than 0.2 micron, ie it is impermeable to microorganisms below 0.2 microns. This fabric allows water and hydrogen peroxide vapours to permeate through the channels of the fabric. The channels do not permit passage of bacteria into the chamber and do not permit nebulant to pass out. Kimguard has a hydrostatic repellency of 3.8 kPa (measure of hydrophobicity) and a cross dimensional tensile load of 70 Newtons and a machine directional tensile load of 130 Newtons.

The semi permeable membrane 9 may be any other suitable semi permeable membrane which facilitates the removal of water while being impermeable by micro-organisms and nebulant particles. Other fabrics and membranes which are permeable by water vapour and hydrogen peroxide vapours and impenetrable by bacteria may be used, for example TYVEK™ and SPUNGUARD™ (However, KIMGUARD™ has been found to be 2-3 times more permeable to hydrogen peroxide vapour than TYVEK™ under the conditions in which it is used here. As will be discussed hereinafter other semi permeable membrane materials such as NAFION™ (which is hydrophilic) and the like may also be employed.

NAFION™ is a copolymer of tetrafluoroethylene and perfluoro 3, 6, dioxa-4-methyl-octene-sulphonic acid. Such materials are hydrophilic and have a very high water of hydration. NAFION™ is able to absorb 22% by weight of water. In this variation the absorption proceeds as a first order kinetic reaction. Water molecules pass through the membrane and then evaporate into the surrounding air until equilibrium with the external humidity is reached in a continuous process called pervaporation. An exterior current flow of air over the external side of the membrane provides rapid removal of the moisture from the outside surface and speeds the pervaporation process. Unlike simple permeation wherein the molecules merely diffuse through the open pores, in pervaporation the membrane is active in selectively drawing molecules from one side of the membrane to the other, and may do so at differential rates for differing types of chemical molecule.

In the embodiments described above the sterilizing agent is a solution of hydrogen peroxide as a 35 wt % solution in water which acted as the solvent. Water is the preferred solvent for use with peroxide. Water boils at 100° C. while hydrogen peroxide boils at above 151° C. at atmospheric pressure. Hydrogen peroxide boils at 151.4° C. at 760 mm. FIG. 1 taken from U.S. Pat. No. 4,797,255 shows (curve A) how the boiling point at atmospheric pressure of a water/peroxide mixture changes with concentration and (curve B) how the gas composition changes. As is shown, pure water boils at 100° C. at atmospheric pressure. It is evident from FIG. 1 that the concentration of hydrogen peroxide in the vapour at below 100° C. is negligible at atmospheric pressure. The solvent could for example be an aqueous or non-aqueous alcohol chosen in combination with the sterilizing agent to be used. The addition to water of ethyl alcohol results in an azeotropic mixture which lowers the boiling point of the solvent and this enables the water to be "flashed" off at lower temperatures than would otherwise be possible. The addition of other azeotropic agents would be equally beneficial. The use of azeotropes to facilitate the removal of solvent from the nebulant solution particles is within the scope of the invention. It is envisaged that for some biocides non-aqueous solvents or a combination of suitable solvents could be employed.

In the case of hydrogen peroxide, as the water flashes off, the concentration of the sterilizing agent increases. If a 35% peroxide solution is used in the invention the micro-nebulant after the heating and water vapour removal steps will have a concentration of for example 60 to 80%. This has the advantage that the starting material can be handled relatively safely, that concentration occurs during the process and that thereafter there is no further need to handle the peroxide. Also, the average particle size is greatly reduced, the micro nebulant particles in preferred embodiments having a mean diameter of less than 1 micron, more preferably less than 0.1 micron. The small particle size results in a very stable suspension with negligible settling out, provides a significant increase in the liquid/gas interfacial area, and in very high concentrations of liquid sterilant per liter of nebulant. The inventors believe that there may be a higher concentration of peroxide molecules at the gas/liquid interface in these nano particles than occurs in micro particles. Solutions of a lower or greater concentration than 35% can be used as a starting material and excellent results have been obtained with hydrogen peroxide solutions of 1% or 3% as well as with solutions of 40%, but the time taken to achieve a satisfactory result with mated or occluded surfaces was less than optimum with peroxide concentrations below 30%, and handling issues result in a preference for concentrations of below 35%. While preferred embodiments described have employed aqueous solutions of hydrogen peroxide as the sterilizing agent, solutions of other peroxides and peroxy compounds can be employed as well as solutions of peroxy complexes (including non water soluble complexes in organic solvents). Sterilizing agents other than peroxides may also be used in the invention, including without limitation halo compounds, phenolic compounds, halogen phenolic compounds and other known biocides, with appropriate choice of solvent.

Whilst concentrations of peroxide in droplets produced from 30-35% peroxide solution typically approach 60% or upwards, it is not always necessary that such a high peroxide concentration is achieved. For example, in other preferred embodiments, a starting solution which has a concentration of 10 to 15% peroxide is nebulised and concentrated to around 45 to 60% peroxide. Any starting concentration of peroxide can be used, and concentrated to any level up to the theoretical maximum achievable under the prevailing conditions of relative humidity and temperature. Generally, in practical terms, a peroxide concentration of 10-15% to 30-35% is employed as the starting solution, which is concentrated up to 45-60% or above in the nebulant.

In an example in which the article to be disinfected is the part of an ultrasonic probe 20, for example a probe of a type insertable into a body cavity for diagnostic purposes, the part of the probe 20 to be treated is enclosed in a chamber 2 (as exemplified in FIG. 9). In this case the chamber is a specially shaped chamber designed so that the whole article need not be in the chamber, only that part of the probe which is to be treated being enclosed. The probe can be suspended inside the chamber by means of a seal around the gland where the power cord enters the probe.

The nano-nebulant is then transported into chamber 2 where it is applied to a target surface. The ultrasound device may be inserted into the chamber via any of the panels on the device. One possible entrance is from the top via a screw top lid into which the cord of the device is clamped and held in place on insertion into the chamber. Passage of the nano-nebulant from the concentrator to the chamber is regulated by a check valve 5. Check valves 5 and 12 can control whether the device operates batchwise, continuously or by some combination of both.

If the device operates batchwise, the valve 5 is opened at the appropriate time after the concentration has occurred.

If the device is operated continuously, the valve remains open, with the flow rates and residence times of the nebulant calibrated beforehand to be at a maximum when exiting the chamber.

Typically, the chamber 2 is constructed of a heat conductive metal such as stainless steel or aluminium. Various coating may be applied to the interior of the chamber such as Teflon to reduce the risk of peroxide breakdown. The disinfection chamber is electrically heated using heater trace wire applied to the conductive metal surface. Alternatively, or in addition, heated air can be blown into chamber. Chamber atmosphere to supply the blower is made-up from another chamber connection which is placed on the opposite side of the chamber to the inlet. The chamber itself is isolated from the generation and recirculation circuit by means of valves which engage once the nano-nebulant cycle is complete (about 1-1.5 min). This isolation from the adjoining circuit is called "suspended time" or more commonly "hold" time.

The surface of the object 1 to be treated with the nebulant is exposed to the nano-nebulant particles for a time sufficient to sterilize the surface. Surprisingly, it has been found that the resulting nano-nebulant is not only more rapidly effective than prior art aerosols, but also is highly effective at penetrating mated surfaces, and treating occluded surfaces which are not directly exposed. While it is not clear why this is so, it may be that a very high density of nano-nebulant (for example 2.0 mg/l or greater at 40% RH) is distributed throughout the volume of the sterilization chamber while at the same time there is little or no actual condensation on the surface. The nano-nebulant particles have a far greater surface area at the gas/liquids interface than the original micro nebulant particles and are significantly smaller in diameter, and consequently remain suspended for much longer periods. Without wishing to be bound by theory, the present applicants believe that the nano-particles impinge on the surface at a greater frequency than the prior art micro particles, and have a longer residence time on the surface than vapour molecules. In comparison with prior art aerosol processes, surfaces treated by the invention may be rapidly dried and are relatively uncontaminated by residual peroxide. When treating a lumen, it is preferred that the lumen be connected to receive a flow of the nebulant through the lumen. Desirably, the external and mated surfaces are also exposed to the nebulant in the chamber or cassette.

The chamber 2 may be formed fully of a semi permeable membrane or fabric or may have a wall of which at least a part is a semi permeable membrane or fabric may be of any suitable shape and design having regard to the requirements of the process herein described and can be sealed in any manner impenetrable by micro organisms. Other semi permeable membranes or fabrics can be selected based on the teaching herein provided. The container may be permanently connected to the nebulizer circuit or may be able to be connected and disconnected by a tube and spigot connection, by suitable connectors or other means.

Once the suspended time is complete (approx 1-2 mins), the system moves into catalytic destruction mode or simply "empty". It is in this cycle that a suction fan engages which pilots (opens under pressure) a check valve that connects to the chamber while another valve allows fresh air to enter the chamber at a controlled rate. This cycle moves the nano-nebulant into the catalytic destructor module where a catalyst is used to convert the hydrogen peroxide into harmless water vapor and oxygen. The catalytic destructor module is composed of metal oxide baked ceramic honeycomb layers sandwiching similarly treated ceramic beads packaged in a suitable container. The amount of catalyst is proportional to the amount of peroxide extracted from the chamber as well as the flow rate from the chamber. Completion of this cycle takes approximately 1 minute and upon completion, the chamber may be accessed to retrieve the disinfected target device. In this configuration the total cycle time for high level disinfection approximates 5 minutes or less. It is understood that the time to achieve sterilization is more onerous and may take significantly longer.

In some preferred embodiments, the droplet density in the aerosol passing from the preconcentrator to the sterilization chamber may be measured by passing an infra red beam across the connecting conduit to a detector and measuring the beam attenuation. This varies with aerosol droplet density and gives a measure of the quantity of peroxide liquid/unit time entering the sterilization chamber. The infra red is preferably of a frequency which is not absorbed by peroxide per se and thus does not register peroxide vapour if any. A knowledge of the aerosol density, temperature and residence time allows certification of the result if desired.

The preconcentrator can be operated in such a manner that it always outputs nebulant comprising peroxide at a predetermined theoretical maximum concentration, thereby avoiding the need to determine the concentration of peroxide at any point of the sterilizing process.

EXAMPLES

Figure 8:
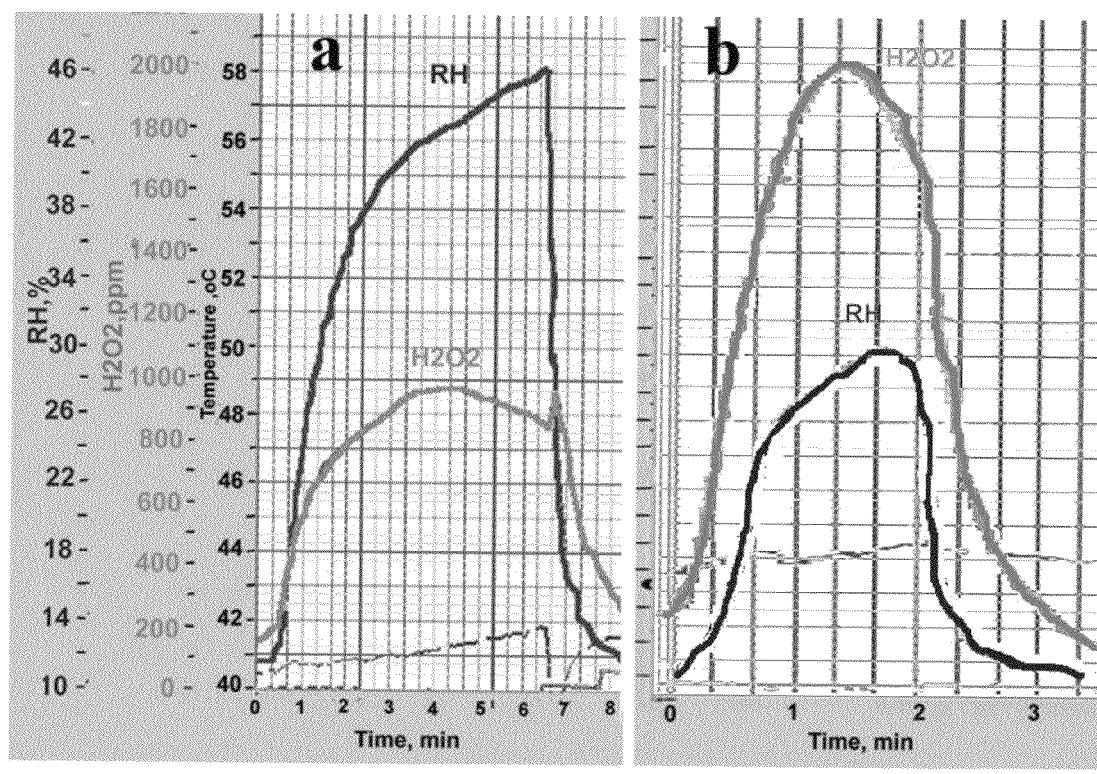
FIG. 8 shows results from a membrane concentrator of the present invention.
Figure 9:
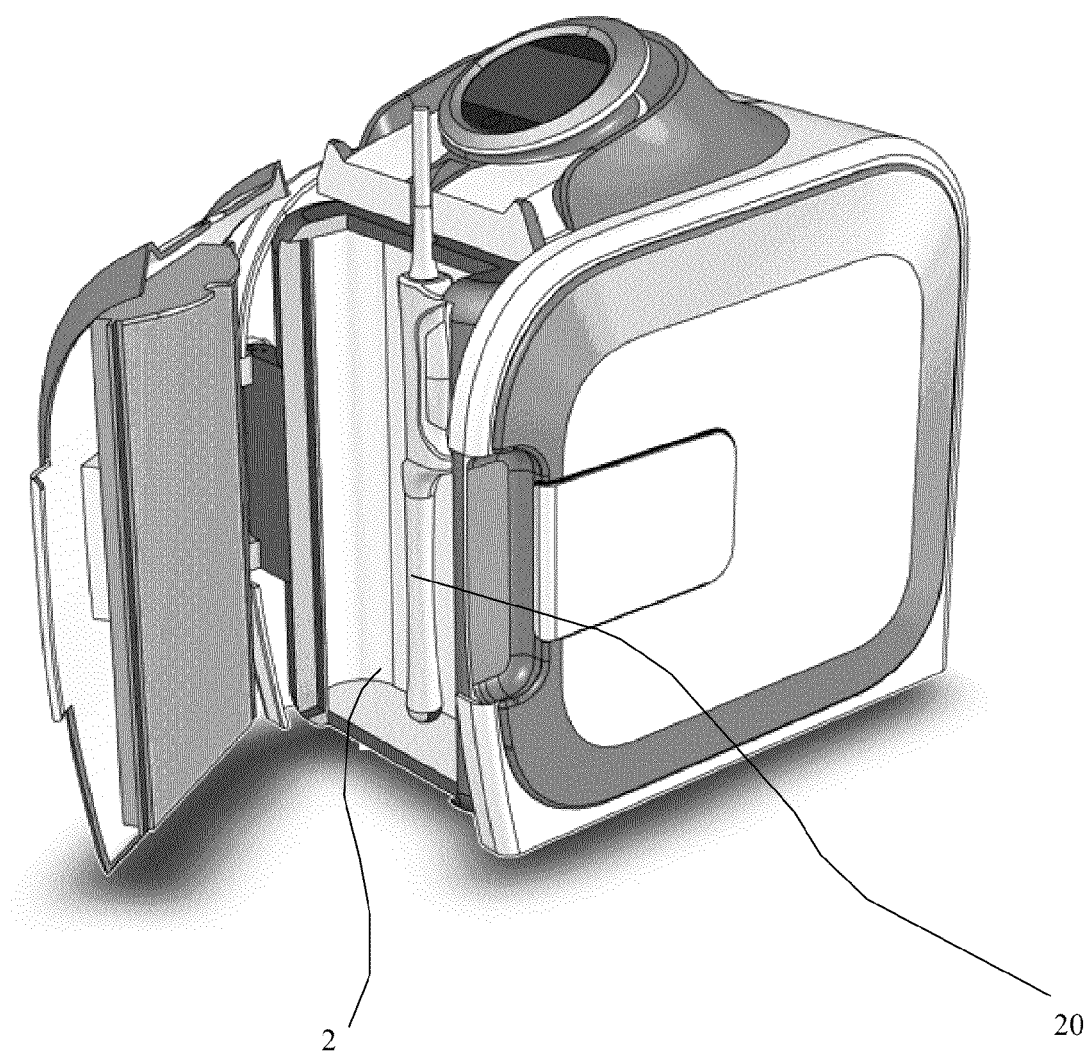
FIG. 9 shows an ultrasonic probe in disinfecting arrangement with a nebuliser of the present invention.

FIG. 8 shows the resulting concentration of peroxide following the use of the membrane concentrator of the present invention. FIG. 8 compares % relative humidity (RH) and peroxide ($H_2O_2$) levels (ppm) measured within a 3 liter chamber with a flow rate of aerosol at 9 l/min into the membrane concentrator described above, or bypassing it entirely. The starting concentration of peroxide was 30%. The membrane used in this case was KIMGUARD although similar profiles are obtained with NAFION and TYVEK.

Bypassing the membrane concentrator/module (FIG. 8a) reveals 46% relative humidity and a peroxide level of about 980 ppm.

However, when the membrane concentrator is employed, it can be seen (FIG. 8b) that the corresponding concentration of peroxide is over 2100, and the relative humidity dropped to 28%. In effect, the use of the pre-concentrator of the present invention has removed a large amount of the water, leading to more than doubling of the peroxide concentration Tables 1, 2 and 3 below indicate that increasing the counter flow results in increased the concentration of peroxide in the 3 L chamber over a 5 minute period with NAFION showing the greatest effect.

TABLE 1

Influence of counter-flow velocity in NAFION membrane module on ratio between hydrogen peroxide and water by weight in disinfection chamber at 50° C.

| Condition of nebulant/ nano-nebulant supply | Velocity of counter-flow L/min | Ratio $H_2O_2/H_2O$ |
| --- | --- | --- |
| Bypasses concentrator | N/A | 0.033 |
| Through concentrator | 0.0 | 0.061 |
|  | 4.5 | 0.108 |
|  | 7.5 | 0.118 |
|  | 9.0 | 0.088 |
|  | 12.0 | 0.102 |

TABLE 2

Influence of counter-flow velocity in TYVEK membrane module on ratio between hydrogen peroxide and water by weight in disinfection chamber at 50° C.

| Condition of nebulant/ nano-nebulant supply | Velocity of counter-flow L/min | Ratio $H_2O_2/H_2O$ |
| --- | --- | --- |
| Bypasses concentrator | N/A | 0.033 |
| Through concentrator | 0.0 | 0.046 |
|  | 4.5 | 0.083 |
|  | 7.5 | 0.082 |
|  | 9.0 | 0.080 |
|  | 12.0 | 0.58 |

TABLE 3

Influence of counter-flow velocity in KIMGUARD membrane module on ratio between hydrogen peroxide and water by weight in disinfection chamber at 50° C.

| Condition of nebulant/<br>nano-nebulant supply | Velocity of counter-flow<br>L/min | Ratio $H_2O_2/H_2O$ |
|---|---|---|
| Bypasses concentrator | N/A | 0.053 |
| Through concentrator | 0.0 | 0.063 |
|  | 4.5 | 0.112 |
|  | 7.5 | 0.149 |
|  | 9.0 | 0.125 |
|  | 12.0 | 0.109 |

Table 4 below indicates the effect of the nano-nebulant process using the membrane concentrator on carriers inoculated with $5\times10^6$ cfu *B. stearothermophilus*/carrier with 400 ppm hard water and 5% horse serum. Flow rate of aerosol was 9 l/min, counter flow was 9 l/min, temperature in the chamber was 50° C. and starting concentration of peroxide was 30%. Peroxide delivered was 0.11 g/l.

TABLE 4

Relationship of time to Spore Reduction on different surface conditions.

| cfu/<br>carrier | Time of<br>exposure<br>(min) | Porcelain<br>penicylinders<br>(log reduction)<br>n = 50 | Stainless steel<br>washers<br>(log reduction)<br>n = 10 | Stainless steel<br>mated<br>washers 85 mm²<br>(log reduction)<br>n = 3 |
|---|---|---|---|---|
| $5 \times 10^6$ | 1 | 2.6 | 5.9 | 2.1 |
| $5 \times 10^6$ | 2 | 5.8 | >6 | 4.3 |
| $5 \times 10^6$ | 5 | >6 | >6 | 5.2 |
| $5 \times 10^6$ | 10 | >6 | >6 | >6 |

The following are illustrative of the types of particle sizes that can be obtained by the pre-concentrators of the present invention. Table 5 shows the particle size distribution of a nebulant from an ultrasonic nebulizer fed with 30% hydrogen peroxide solution at various temperatures. These would represent the input particle sizes for the pre-concentrators of the present invention.

TABLE 5

| Heater's<br>outlet T<br>° C. | 10% below<br>(particle size, μm) | 50% below<br>(particle size, μm) | 90% below<br>(particle size, μm) |
|---|---|---|---|
| 25 | 2.84 | 5.5 | 9.48 |
| 55 | 0.95 | 1.36 | 2.0 |
| 60 | 0.58 | 0.86 | 1.36 |

Table 6 shows the particle size data at 25° C. of the nebulant when a NAFION membrane was used with various airflow rates on the exterior side.

TABLE 6

| Counter<br>flow m/s | 10% below<br>(particle size, μm) | 50% below<br>(particle size, μm) | 90% below<br>(particle size, μm) |
|---|---|---|---|
| 0 | 2.29 | 4.61 | 8.58 |
| 3.2 | 2.33 | 3.99 | 6.36 |
| 7.5 | 2.0 | 2.9 | 3.96 |

Table 7 shows the particle size data at 25° C. of the nebulant when a KIMGUARD membrane was used at various flow air flow rates on the exterior side.

TABLE 7

| Counter<br>flow m/s | 10% below<br>(particle size, μm) | 50% below<br>(particle size, μm) | 90% below<br>(particle size, μm) |
|---|---|---|---|
| 0 | 2.29 | 4.61 | 8.58 |
| 3.2 | 2.31 | 4.17 | 7.2 |
| 7.5 | 2.57 | 4.2 | 6.51 |

Particle size can be seen to have dropped by about half in the case of Nafion (corresponding to a droplet volume reduction to about 30% original size) and about one third in the case of Kimguard (corresponding to a droplet volume reduction to about 13% original size).

Although the invention has been herein described with reference to hydrogen peroxide as the sterilizing agent, the invention could use other peroxides, peroxy-compounds, or complexes of either. Other classes of biocide could be used including without limitation halogenated biocides, phenolic biocides and quaternary compound biocides and it may be advantageous to use solvents other than water. Likewise, although the invention has been herein exemplified primarily with reference to starting solutions having 35% peroxide, other starting concentrations can be employed, although concentrations between about 20% and 35% are preferred.

The principles herein taught could be applied to concentrate the peroxide in such vapour processes by permeation or pervaporation through a membrane, without the need for pressure reduction. However the benefits (described in our co-pending application) of utilizing the aerosol of the invention would be lost as a sterilant would be lost.

The invention claimed is:

1. A method for concentrating a nebulant to produce a concentrated nebulant and wherein the concentrated nebulant is used to disinfect and/or sterilize an article, the method comprising:
   (1) providing a flow of a nebulant consisting of a biocide in a solvent and having a first biocide:solvent ratio to a first side of a gas permeable membrane; and
   (2) providing a counter-flow of a gas to a second side of the gas-permeable membrane whereby to increase said first biocide:solvent ratio on the first side to a second biocide:solvent ratio greater than the first biocide:solvent ratio.

2. A method according to claim 1 wherein the solvent is water.

3. A method according to claim 1 wherein the biocide is selected from the group consisting of hydrogen peroxide or a peroxy compound.

4. A method according to claim 1 wherein the first biocide to solvent ratio is below 35 wt %.

5. A method according to claim 1 wherein the second biocide:solvent ratio is above 60 wt %.

6. A method according to claim 1 wherein the counter-flow of gas is provided at a rate and for a time such that the second biocide:solvent ratio reaches an equilibrium ratio beyond which it will not increase.

7. A method according to claim 1 wherein the gas is air or humidity conditioned air.

8. A method according to claim 1 wherein the semi permeable fabric or membrane is a woven, or non-woven fabric, or a sheet or film or a combination thereof and of a single layer or multilayer construction.

9. A method according to claim 1 wherein the semi permeable membrane is hydrophobic.

10. A method according to claim 1 wherein the semi permeable membrane is selected to ensure that nebulant particles at the first biocide:solvent ratio are initially unable to permeate there through.

11. A method according to claim 1 wherein the membrane is suitable for pervaporation.

12. A method according to claim 1 wherein the nebulant is an aqueous peroxide solution having an initial concentration of from 6 wt %-35 wt % of peroxide.

13. A method according to claim 12 wherein the solution is nebulized in an ultrasonic nebulizer operated at greater than 2.0 MHz and which generates an aerosol in which particles having a size range distribution of about 1-10 microns are suspended in an air stream.

14. A method according to claim 1 wherein the semi permeable membrane is selected to remove one or more vapours by a process of pervaporation.

15. A method according to claim 1 wherein the nebulant at the first biocide:solvent ratio has 90% of particles in the 3-5 μm range.

16. A method according to claim 1 wherein the nebulant at the second biocide:solvent ratio has an average particle diameter of less than 1.0 micron.

* * * * *